United States Patent [19]

Jones et al.

[11] 4,096,875
[45] Jun. 27, 1978

[54] PRESSURE FLUID-ACTUATED OSCILLATOR

[75] Inventors: Norman Stewart Jones, Leighton Buzzard; Geoffrey Richard Bennett, Linslade, both of England

[73] Assignee: Pneupac Limited, London, England

[21] Appl. No.: 664,185

[22] Filed: Mar. 5, 1976

[30] Foreign Application Priority Data

Mar. 7, 1975 United Kingdom ............... 9697/75

[51] Int. Cl.$^2$ ............................................. A61M 16/00
[52] U.S. Cl. ............................... 137/102; 137/624.14; 91/308
[58] Field of Search ............... 137/624.14, 119, 106, 137/102; 91/308; 235/201 ME; 128/185

[56] References Cited

U.S. PATENT DOCUMENTS

| | | | |
|---|---|---|---|
| 2,698,517 | 1/1955 | Witt | 91/308 |
| 2,711,717 | 6/1955 | Stacey | 91/308 X |
| 3,225,663 | 12/1965 | Pelisson | 91/308 X |
| 3,614,965 | 10/1971 | Metivier | 137/624.14 X |

Primary Examiner—Alan Cohan
Attorney, Agent, or Firm—Kurt Kelman

[57] ABSTRACT

A pressure fluid-actuated oscillator, especially suitable for use in lung ventilation equipment for emergency use, comprises a double-piloted 5-port valve and biased timer valves controlling the supply to its pilots to provide for repeated changeover of the 5-port valve at intervals determined by the respective timing periods of the timer valves. One of the timer valves has an adjustable timing period whereas the other has a nominally fixed timing period but is made sensitive to the duration of the immediately preceding timing period determined by the adjustable timer valve so as automatically to change its timing period in the same sense as adjustment of the adjustable timer valve.

In lung ventilation equipment using such an oscillator, therefore, a single control may serve for directly setting the critical inhalation phase duration and to cause a complementary alteration of the exhalation phase duration that maintains the ratio of duration of the respective phases within desirably close limits.

6 Claims, 1 Drawing Figure

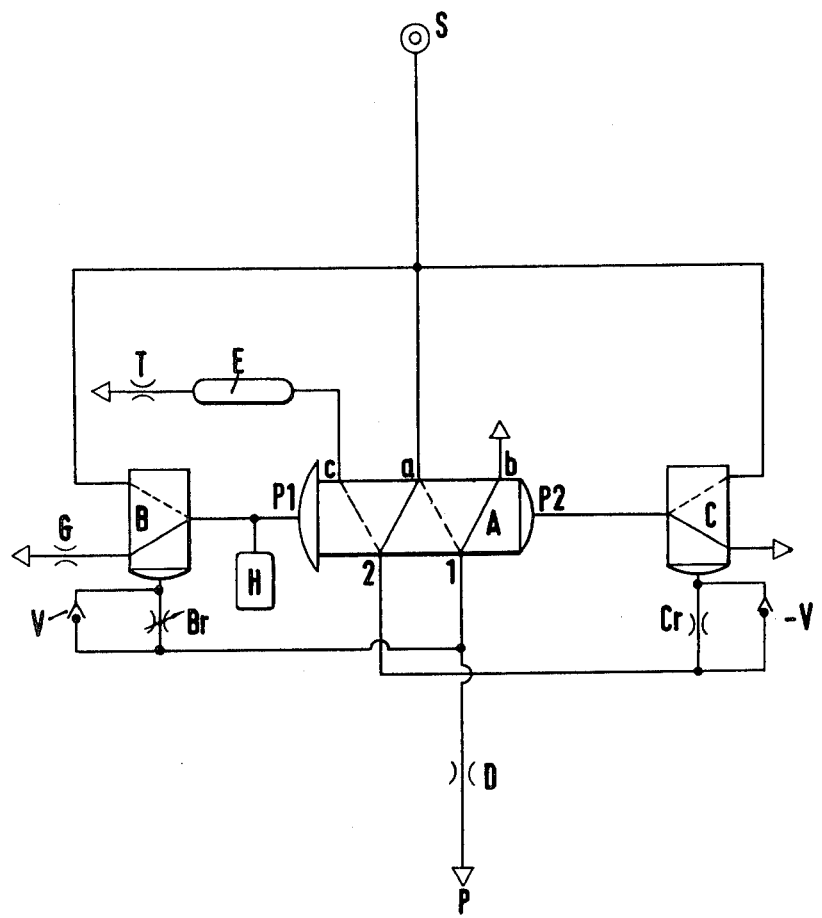

PRESSURE FLUID-ACTUATED OSCILLATOR

FIELD OF THE INVENTION

This invention concerns pressure fluid-actuated oscillators and especially oscillators adapted to be powered by a compressed breathable gas such as air or oxygen (or an anaesthetic gas mixture) in lung ventilation equipment.

BACKGROUND TO THE INVENTION

A typical pneumatic oscillator for lung ventilation equipment comprises a 5-port double-piloted relay valve having its pilot ports fed respectively through timer valves biased against pilot pressure that is derived from the respective outlets of the 5-port valve. The arrangement is such that when the 5-port valve is in one stroke end position connecting a pressure source to one of its two outlets, that outlet feeds pilot pressure to one of the timer valves; when either timer valve is changed over ("fired") in response to application or release of such pilot pressure, (depending on the timer valve type) it applies pilot pressure to displace the spool of the 5-port valve to its other stroke end position. In an oscillator of this type, the 5-port valve changes over repeatedly at successive intervals determined by the respective settings of the timing intervals of the two timer valves.

An important application of pneumatic oscillators of this general type is in lung ventilation equipment intended for emergency use by ambulance or rescue service personnel, the oscillator being powered by breathable gas from a portable source such as a cylinder of compressed gas and serving to control the delivery at suitable intervals of gas pressure pulses each consisting of a respiration tidal volume of the breathable gas. Lung ventilation equipment for such purposes should be as simple as possible to operate and control by relatively unskilled personnel. Thus its controls should be as simple as possible while yet providing for adequate adjustment of operating characteristics to suit the requirements (e.g. respiration tidal volume, respiration rate and so on) of a particular patient.

Apart from some form of on/off control device it is generally necessary to provide some means of adjusting the period of oscillation of the oscillator so as thereby to adjust, at least, the repetition rate of the pulses of breathable gas supplied to a patient by the equipment, and also, usually a means for adjusting the tidal volume of each pulse.

As has been explained above, the typical oscillator has two timer valves the timing periods of which respectively determine the alternating "mark" and "space" durations within an operating cycle of the oscillator; that is to say, in lung ventilation equipment having such an oscillator, one timer valve determines the duration of the inhalation phase during which the equipment delivers breathable gas to the patient while the other timer valve determines the duration of the subsequent exhalation phase.

It is, of course, possible to provide independent controls for adjusting each of the timer valves so that the equipment can be set to operate at a desired pulse repetition (respiration) rate with the cycle divided as desired between inhalation and exhalation phases. However, the trend of design is to avoid the complication of separate controls for inhalation and exhalation phase duration, thereby to simplify control of the equipment and to minimise the risk of inappropriate ratios of inhalation/exhalation phase duration being selected by an operator working in a hostile environment or under other adverse conditions. Thus the trend of design has been to fix the duration of the exhalation phase by a fixed setting of the relevant timer valve and to provide only control of the inhalation phase duration by providing for adjustment of the timing period of the related timer valve, thus achieving related adjustment of respiration rate and tidal volume by the operation of a single control.

The disadvantage of this control simplification, however, is that the ratio of duration of the inhalation phase to the exhalation phase varies with the setting of the control determining the inhalation phase duration and, thus, the overall cycle duration. In natural breathing the duration ratio is about 1:2 but it is found that by providing only for control of inhalation phase duration in a cycle having a fixed exhalation phase duration, the ratio may range from about 1:1.6 to about 1:10 in the case of equipment having an adequate range of overall cycle duration control.

An object of the present invention is, therefore, to provide a pressure fluid-actuated, e.g. a pneumatic, oscillator having control arrangements that enable a direct adjustment of the duration of one phase of the oscillator cycle to effect a complementary adjustment of the duration of the other phase and so avoid excessive variation of the ratio of durations of the respective phases.

SUMMARY OF THE INVENTION

A pressure fluid-actuated oscillator in accordance with the present invention comprises a double-piloted 5-port valve and biased timer valves connected, as usual, to the outlets of the 5-port valve to control the application of pilot pressure to the pilot ports of the 5-port valve in an arrangement providing for repeated change over of the 5-port valve at intervals determined by the respective timing periods of the timer valves. Control means are provided for directly adjusting the timing period of one timer valve thereby directly to adjust the oscillation phase duration controlled by the timer valve. However, the other timer valve is non-adjustable in normal operation but is arranged to have is timing period affected by the duration of the oscillation part-cycle preceding the commencement of the timing period.

As has been explained, in an oscillator of the general type comprising a 5-port valve associated with biased timer valves controlling the supply of pilot pressure to the pilot ports of the 5-port valve, the individual timer valves respectively control the duration of the alternate part-cycles of the overall oscillation cycle: that is to say one timer valve controls the "mark" duration whereas the other controls the "space" duration. Accordingly in an oscillator in accordance with the invention the duration of one part-cycle is directly controlled by adjustment of its related timer valve while the duration of the other part-cycle is determined jointly by the setting of its related timer valve and the duration of the preceding part-cycle as determined by the setting of the timing period of the directly-adjusted timer valve.

For ease of description, the timer valve that is not provided with direct control of its timing period is called the "non-adjustable timer valve" herein but it should be understood that the valve may and usually will be of a construction permitting adjustment of its timing period during manufacture and during the construction and initial calibration of the oscillator, the valve being "non-adjustable" only in the sense that no provision is made for routine adjustment of its timing period in the course of normal usage of the oscillator.

The manner in which the non-adjustable timer valve is adapted to have its timing period affected by the preceding part-cycle duration depends upon the construction of the timer valve and the particular circuitry by which the timer valves are associated with the 5-port valve. Thus if, as is preferred, the timer valves are of the type that measure a timing period from the application of supply pressure to their operating pilot ports, the non-adjustable timer valve may conveniently be made responsive to the preceding partcycle duration by restricting the rate at which pressure may decay at its operating pilot port. Conveniently the exhaust port associated with the 5-port valve outlet connected to such a non-adjustable timer valve operating pilot port may be connected to vent through a throttle instead of merely venting to atmosphere. To achieve a desired time-constant, a capacity may be associated with said exhaust port and throttle.

It should be understood that in an arrangement as above described, the effect of the restriction upon the rate of decay of pressure at the operating pilot port of the non-adjustable timer valve is to make the residual pressure at that port, at the instant of its connection by the 5-port valve to a pressure source, progressively higher as the duration of the preceding part-cycle is shortened: therefore the time required for the pressure on the operating pilot of the timer valve to build up to firing value and effect a change over of the 5-port valve is progressively reduced as the duration of the preceding part-cycle is shortened.

In preferred embodiments of the invention an asymmetrically-piloted 5-port valve having an open-centre supply configuration is employed in accordance with the invention disclosed in our copending Application Ser. No. 632,962 filed Nov. 18, 1975, the non-adjustable timer valve preferably being associated with the smaller effective pilot of such a 5-port valve.

As noted the oscillator of the invention is especially applicable to lung ventilation equipment and in such applications the preferred arrangement is for the non-adjustable timer valve to control the duration of the part-cycle that corresponds with the exhalation phase, and adjustable timer valve controlling the inhalation phase duration and thus controlling the tidal volume of each pulse as well as the pulse repetition rate.

The relationship between a change in the duration of the part-cycle directly controlled by the adjustable timer valve — that is to say, the inhalation phase duration in the case of preferred arrangements applied to lung ventilation equipment — and the alteration of the duration of the partcycle controlled by the non-adjustable timer valve depends upon the construction of the non-adjustable time valve and the manner in which its timing period is affected by the duration of the preceding part-cycle. While exact correspondence may be obtained — that is to say, the arrangement may provide for maintaining a fixed ratio of part-cycle durations — for lung ventilation equipment applications it will usually be preferable to arrange that the relative duration of the exhalation phase increases as the absolute duration of the inhalation phase is decreased. Thus in a typical application of the oscillator of the invention to lung ventilation equipment, the control of the adjustable timer valve may provide for a 6:1 change in the duration of the inhalation phase with a 2:1 change in the duration of the exhalation phase.

THE DRAWING AND DESCRIPTION OF PREFERRED EMBODIMENT

The single FIGURE of the accompanying drawing is a circuit diagram illustrating an oscillator that comprises an asymmetrically-piloted 5-port valve A having an open-centre supply configuration with biased timer valves B and C controlling pilot pressure application to the larger and smaller effective pilots, P1, P2, respectively, of the 5-port valve A. The valve A has an inlet port $a$ connected to a source S of pressure fluid as indicated by the conventional symbol, exhaust ports $b$ and $c$ and outlet ports 1 and 2. Both timer valves B and C are of the type that change over ("fire") after a timing period has elapsed from the application of supply pressure, from an outlet port of the valve A, to a restrictor Br, Cr upstream of an operating pilot and the circuit arrangement is such that firing of either timer valve at the conclusion of its timing period is effective to connect the pressure source S to the associated pilot port P1 or P2, of the 5-port valve.

The restrictor Br of timer valve B is adjustable for direct adjustment of the timing period of the valve B, whereas the timer valve C is non-adjustable in the sense that its restrictor Cr is fixed during manufacture or initial calibration of the oscillator. As shown in the diagram, the restrictors Br, Cr of the timer valve B, C are each bypassed by a non-return valve $v$ permitting unrestricted venting of the operating pilot and it is to be understood that the restrictor and non-return valve of such a timer valve are normally integral parts of the valve construction and the operating pilot port of the valve is the upstream junction between the restrictor and non-return valve.

In accordance with the invention the exhaust port $c$ of the 5-port valve that is associated with the outlet port 2 to which the operating pilot port of the non-adjustable timer valve C is connected, is connected to vent through a throttle T that therefore restricts the rate of decay of pressure at the operating pilot port of the timer valve C when the 5-port valve A is changed over as a result of the firing of the timer valve C. A capacity E is connected between the throttle T and the 5-port valve exhaust port $c$ to provide an appropriate time-constant for this circuit and to achieve prompt and reliable resetting of the valve C as will be explained.

The circuit as illustrated is self-oscillating when supplied with pressure fluid such as a compressed gas. The source S of pressure fluid is represented by the conventional symbol on the line connected to the inlet port $a$ of the 5-port valve A to be connected thereby either to outlet port 1 or outlet port 2 of that valve in accordance with the position of the spool thereof. As noted, the valve A is of open-centre supply configuration so that if it should happen to come to rest in a mid-stroke position, source pressure when reapplied to inlet port $a$ will be directed to both of the outlet ports 1 and 2, and thence to the operating pilot ports of the two timer valves B and C so that both of these will be prepared for the firing after the elapse of their respective timing periods. In this respect the arrangement of the 5-port valve A and the timer valves B and C is in accordance with the invention disclosed in our copending Application Ser. No. 632,962 and in the event of both valves B and C firing simultaneously the larger effective pilot P1 will determine the response of the valve A.

The operating pilot port of the timer valve B is connected to outlet port 1 of the valve A, whereas the operating pilot port of the timer valve C is connected to the outlet port 2 of the valve A. Outlet port 1 of the valve A is also connected to a pulse outlet conduit P via a throttle D. In the case of lung ventilation equipment, the throttle D would preferably be a sonic-flow restrictor for the purposes disclosed in copending Application Ser. No. 632,963 filed Nov. 18, 1975, by one of us, while the pulse outlet conduit P would be connected to an oronasal mask or like device via a suitable patient valve, preferably of the construction disclosed in copending U.S. Pat. No. 4,004,603.

In its alternative stroke-end positions, the 5-port valve A sets up the connections shown in broken and full lines respectively. The stroke-end position giving the full line connections is that obtained by the application of source pressure to the larger effective pilot P1 of the valve A (or to both of its pilots under certain fault conditions as more fully explained in our copending Application Ser. No. 632,962) and in this stroke end position the pressure fluid source S is connected to the outlet port 2 and thus to the operating pilot port of the timer valve C, but is disconnected from the outlet port 1, from the pulse output conduit P and from the operating pilot port of the timer valve B.

When the 5-port valve A is moved to the stroke-end position giving the broken line connections by the application of source pressure to the smaller effective pilot P2, the source S is connected to the outlet port 1 and a timing period determined by the setting of the adjustable restrictor Br of the timer valve B commences to elapse. At the conclusion of this timing period, the timer valve B fires to connect the pressure fluid source to the larger effective pilot P1 of the valve A and thus effects a change over of that valve to its other stroke end position in which the connections are as shown by the full lines. In this latter stroke end position, the outlet port 1 of the valve A is connected to exhaust port $b$ so that pressure at the operating pilot port of the timer valve B may decay and allow the valve B to reset.

As soon as the valve A changes over as a result of the firing of timer valve B, source pressure is applied to the outlet port 2 and thus to the operating pilot port of the non-adjustable timer valve C. After a timing period determined by the calibration of this valve, the valve C fires to apply source pressure to the smaller effective pilot of the valve A, thus causing this valve to revert to its former stroke-end position with the pressure fluid source connected to the outlet port 1 as indicated by the broken line connections. The cycle then repeats in the manner described.

While the valve A is in the stroke-end position in which the pressure source is connected to the outlet port 1 as described above, the operating pilot port of the timer valve C is connected to exhaust via the capacity E and the throttle T: accordingly pressure at the operating pilot port of this timer valve decays at a rate determined by the time-constant of the circuit. However, because of the presence of the capacity E, the pressure at first falls sharply while the capacity E is charging and this sharp initial fall of pressure at the operating pilot port of the timer valve C causes this valve to reset almost immediately, whereby the smaller effective pilot P2 of the valve A is promptly connected to exhaust to permit unimpeded change over of the valve A upon subsequent firing of the timer valve B.

At the instant that the timer valve B fires to effect change over of the 5-port valve A as explained, the residual pressure at the operating pilot port of the timer valve C will depend upon the duration of the part-cycle in which the port was connected to exhaust through the capacity E and throttle T. The shorter this part-cycle duration, the higher will be the residual pressure at the operating pilot of the timer valve C when the timer valve B fires, and therefore the less time that will be required, following change over of the valve A, for pressure at the pilot of valve C to build up again to firing value.

Thus as the pulse duration at the pulse outlet conduit P is shortened by adjustment of the adjustable restrictor Br of the timer valve B, so will the effective timing period of the timer valve C be shortened to shorten the inter-pulse period.

As noted, the capacity E serves to ensure a rapid initial drop of pressure at the operating pilot of the timer valve C upon change over of the valve A as a result of firing of the valve C, and this ensures prompt and reliable resetting of the valve C, notwithstanding variable friction in the latter. However, there is a limit to the value of the capacity E since its presence determines, in conjunction with the throttle T, the residual pressure at the operating port of the timer valve C after any given duration, and required residual pressure/time characteristics may not be obtainable with a sufficiently large capacity E to ensure sufficiently prompt resetting of the valve C under all circumstances.

Thus it could happen that with the timer valve B set to give very short duration pulses on conduit P, the valve C might not have reset within the timing period of valve B so that upon firing of the latter and change over of valve A, valve C would already be in a fired condition, keeping source pressure on the smaller effective pilot of valve A. As a result, the valve A would revert immediately upon resetting of the valve B, instead of after an interval determined by valve C. A rapid oscillation of the valve A could thus be initiated, the valve A changing over in synchronism with the valve B and giving a series of almost unspaced pulses on the conduit P.

To supplement the effect of the capacity E, therefore, and to prevent such type of oscillator action occurring, a throttle G may, as shown, be included in the exhaust circuit for the larger effective pilot P1 of the valve A so that reversion of the valve A under the influence of pressure at pilot P2 is delayed. To ensure an adequate delay, the circuit to pilot P1 may, as shown, include a capacity H so that the valve A will be held for not less than a predetermined interval between pulses on the conduit P for all available settings of the timing period of the valve B.

We claim:

1. A pressure fluid-actuated oscillator comprising
    (a) a double-piloted five-port valve including an inlet port for receiving the pressure fluid, two outlet ports and two exhaust ports;
    (b) two biased timer valves respectively connected to a respective one of the outlet ports to control oscillating change-over between two part-cycles of the five-port valve, the inlet port being in communication with one of the outlet ports during each part-cycle of the oscillating change-over, and the other outlet port being in communication with a respective one of the exhaust ports during each part-cycle, and each of the timer valves being set at a timing period determining the respective part-cycle;

(c) control means for directly adjusting the timing period of one of the timer valves whereby the duration of the part-cycle of the oscillating change-over controlled by the one timer valve is directly adjusted; and (d) means sensitive to the duration of said part-cycle for determining the timing period of the other timer valve.

2. The oscillator of claim 1, said means sensitive to the duration of said part-cycle comprises means restricting the rate of pressure decay at the operating pilot port of the other timer valve.

3. The oscillator of claim 2, wherein the operating pilot port of the other timer valve is connected to one of the outlet ports and a throttle is arranged to restrict venting through the corresponding one of the exhaust ports.

4. The oscillator of claim 3, further comprising a capacity connected between the one exhaust port and the throttle.

5. Lung ventilation equipment comprising an oscillator according to claim 1 and in which the other timer valve controls the inhalation phase duration.

6. Lung ventilation equipment according to claim 5, wherein the control means is capable of adjusting the timing period of the one timer valve through a 6:1 range of duration values and the sensitive means permits the other time valve to respond to variation in the timing period through said value range by a 2:1 change in the duration of the timing period thereof.

* * * * *